(12) United States Patent
McCollum et al.

(10) Patent No.: US 9,850,517 B2
(45) Date of Patent: Dec. 26, 2017

(54) COMPACT AUTOMATED CELL COUNTER

(71) Applicant: Bio-Rad Laboratories, Inc., Hercules, CA (US)

(72) Inventors: Tom McCollum, Berkeley, CA (US); Paul Patt, Hercules, CA (US); Frank Shen, Martinez, CA (US); Daniel Y. Chu, Hercules, CA (US); Don Flory, Hercules, CA (US); Mike Griffin, El Cerrito, CA (US); Xin Heng, Emeryville, CA (US); Eli Hefner, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 587 days.

(21) Appl. No.: 14/039,682

(22) Filed: Sep. 27, 2013

(65) Prior Publication Data

US 2014/0024107 A1    Jan. 23, 2014

Related U.S. Application Data

(62) Division of application No. 12/869,979, filed on Aug. 27, 2010, now Pat. No. 8,570,370.

(Continued)

(51) Int. Cl.
*C12Q 1/06* (2006.01)
*G01N 15/14* (2006.01)
(Continued)

(52) U.S. Cl.
CPC .......... *C12Q 1/06* (2013.01); *G01N 15/1434* (2013.01); *G02B 21/0008* (2013.01); *G02B 21/34* (2013.01)

(58) Field of Classification Search
None
See application file for complete search history.

(56) References Cited

U.S. PATENT DOCUMENTS 3,879,106 A * 4/1975 McCormick .......... G02B 21/34
356/246
5,595,710 A * 1/1997 Van Dusen ............... B01L 9/52
206/455

(Continued)

FOREIGN PATENT DOCUMENTS

JP    H05-133904 A    5/1993
JP    H06-507499 A    8/1994
(Continued)

OTHER PUBLICATIONS

International Search Report from PCT/US2010/047143, dated Oct. 18, 2010, 9 pages.

(Continued)

*Primary Examiner* — Kate Luo
(74) *Attorney, Agent, or Firm* — Kilpatrick Townsend and Stockton LLP (57) ABSTRACT

Biological cells in a liquid suspension are counted in an automated cell counter that focuses an image of the suspension on a digital imaging sensor that contains at least 4,000,000 pixels each having an area of 2×2 μm or less and that images a field of view of at least 3 mm². The sensor enables the counter to compress the optical components into an optical path of less than 20 cm in height when arranged vertically with no changes in direction of the optical path as a whole, and the entire instrument has a footprint of less than 300 cm². Activation of the light source, automated focusing of the sensor image, and digital cell counting are all initiated by the simple insertion of the sample holder into the instrument. The suspension is placed in a sample chamber in the (Continued)

form of a slide that is shaped to ensure proper orientation of the slide in the cell counter.

18 Claims, 5 Drawing Sheets

Related U.S. Application Data (60) Provisional application No. 61/238,534, filed on Aug. 31, 2009.

(51) Int. Cl.
    *G02B 21/34*      (2006.01)
    *G02B 21/00*      (2006.01)

(56) References Cited

U.S. PATENT DOCUMENTS

| | | | |
|---|---|---|---|
| 6,049,421 A | 4/2000 | Raz et al. | |
| 6,459,747 B1 * | 10/2002 | van Geel | G01T 5/00 |
| | | | 250/472.1 |
| 6,640,014 B1 | 10/2003 | Price et al. | |
| 6,975,400 B2 | 12/2005 | Ortyn et al. | |
| 7,109,481 B1 * | 9/2006 | Zanon | H01J 49/0418 |
| | | | 250/281 |
| 7,411,680 B2 | 8/2008 | Chang et al. | |
| 7,428,324 B2 | 9/2008 | Crandall et al. | |
| 7,499,166 B2 | 3/2009 | Albertson et al. | |
| 7,546,210 B2 | 6/2009 | Callahan et al. | |
| 8,570,370 B2 | 10/2013 | McCollum et al. | |
| 2002/0171750 A1 | 11/2002 | Kato | |
| 2003/0026762 A1 | 2/2003 | Malmros et al. | |
| 2003/0094751 A1 | 5/2003 | Takei | |
| 2003/0104588 A1 * | 6/2003 | Orwar | A61K 9/127 |
| | | | 435/173.6 |
| 2004/0170312 A1 | 9/2004 | Soenksen | |
| 2006/0192081 A1 | 8/2006 | Cartlidge et al. | |
| 2006/0223165 A1 | 10/2006 | Chang et al. | |
| 2007/0077549 A1 | 4/2007 | Buller et al. | |
| 2007/0078254 A1 | 4/2007 | Matsumoto et al. | |
| 2007/0174653 A1 * | 7/2007 | Berman | G01N 35/00623 |
| | | | 714/2 |
| 2008/0019584 A1 | 1/2008 | Lindberg et al. | |
| 2008/0088952 A1 | 4/2008 | Unger et al. | |
| 2008/0137938 A1 | 6/2008 | Zahniser | |
| 2008/0239515 A1 | 10/2008 | Asami et al. | |
| 2012/0295300 A1 | 11/2012 | Heng et al. | |

FOREIGN PATENT DOCUMENTS

| | | |
|---|---|---|
| JP | 07-083817 A | 3/1995 |
| JP | 2000-501829 A | 2/2000 |
| JP | 2001-174456 A2 | 6/2001 |
| JP | 2003-015016 A2 | 1/2003 |
| JP | 2003-323600 A2 | 11/2003 |
| JP | 2005-121967 A2 | 5/2005 |
| JP | 2005-524072 T2 | 8/2005 |
| JP | 2006-519365 T2 | 8/2006 |
| JP | 2006-322765 A2 | 11/2006 |
| JP | 2006-524818 T2 | 11/2006 |
| JP | 2008-539724 T2 | 11/2006 |
| JP | 2007-134968 A2 | 5/2007 |
| JP | 2009-135318 A2 | 11/2007 |
| JP | 2008-502027 A | 1/2008 |
| JP | 2008-096407 A2 | 4/2008 |
| JP | 2008-129512 A2 | 6/2008 |
| JP | 2009-075131 A2 | 4/2009 |
| JP | 2009-128267 A2 | 6/2009 |
| JP | 2009-174966 A2 | 8/2009 |
| WO | 2005/121864 A2 | 12/2005 |
| WO | 2009/107321 A1 | 9/2009 |

OTHER PUBLICATIONS

Notice of Reasons for Rejection dated May 29, 2013, from Japanese Application No. 2012-527068 (8 pages).
Supplementary European Search Report from EP 10812708.5, dated Jun. 10, 2014.

\* cited by examiner

COMPACT AUTOMATED CELL COUNTER

CROSS-REFERENCE TO RELATED APPLICATION

This application is a divisional of U.S. patent application Ser. No. 12/869,979, filed Aug. 27, 2010, which claims the benefit of U.S. Provisional Patent Application No. 61/238,534, filed Aug. 31, 2009, the contents of which are incorporated herein by reference.

BACKGROUND OF THE INVENTION

1. Field of the Invention

This invention lies in the field of hemocytometry and systems in general for the counting of biological cells suspended in fluids. The focus of this invention is on automated cell counting systems.

2. Description of the Prior Art

Cell counting is of interest in a variety of clinical and research procedures, including the counting of leukocytes and erythrocytes, which is of value in the diagnosis of various diseases or abnormal conditions and in the monitoring of patients that are undergoing treatment for such diseases or conditions. Cells can be counted manually by placing a known dilution of a sample between optically clear plates that are sufficiently close to each other (typically with a spacing on the order of 100 microns) to form the cells into a single layer, magnifying an area of the layer of designated dimensions to a known magnification, and counting the cells in the magnified area through a microscope. Manual cell counters often include a grid inscribed in the counting area to lessen the burden on the user. A description of such a grid and the procedure for its use is found in Qiu, J., U.S. Pat. No. 7,329,537 B2, issued Feb. 12, 2008, "Micro-Pattern Embedded Plastic Optical Film Device for Cell-Based Assays." Regardless of how it is done, manual cell counting is tedious and highly vulnerable to user error. Counting is commonly aided by using a high dilution of the sample to lessen the number of cells in the counting area, but the accuracy of the counting declines with every decrease in the proportion of cells that are counted.

Automation of cell counting procedures has been made possible by the use of digital imaging systems. An example of such a system is ImageJ, a Java-based image processing program developed at the National Institutes of Health and reported by Collins, T. J., "ImageJ for microscopy," *BioTechniques* 43 (1 Suppl.): 25-30 (July 2007). The use of ImageJ in hematology systems is reported by Gering, T. E., and C. Atkinson, "A rapid method for counting nucleated erythrocytes on stained blood smears by digital image analysis," *J. Parasitol.* 90(4): 879-81 (2004). Further disclosures of automated cell counting are Chang, J. K., et al., U.S. Pat. No. 7,411,680 B2, issued Aug. 12, 2008, "Device for Counting Micro Particles," and Chang, J. K., et al., United States Patent Application Publication No. US 2006/0223165 A1, published Oct. 5, 2006, "Device for Counting Cells and Method for Manufacturing the Same."

Automated cell counting systems themselves contain an inherent statistical uncertainty due to what is commonly referred to as "sampling error," which refers to the error inherent in selecting the area in which the automated counting is performed. One of the limitations of automated cell counters that are currently available is that due to the limitations of the optical components in the instruments, the area in which cells are counted is of limited size compared to the entire area occupied by the sample. Since this limits the number of cells accordingly, and the error increases with every decrease in the number of cells being counted, the typical instrument of the prior art is constructed with a long optical path or a large footprint (the surface area on a laboratory bench that the instrument consumes), or both, to achieve an acceptable level of accuracy. This presents disadvantages to the user, particularly when the instrument is to be used in a cell culture hood.

SUMMARY OF THE INVENTION

Disclosed herein is a fully self-contained instrument for highly accurate cell counting with minimal user intervention as well as a relatively small footprint and limited height. A cell suspension is placed in a consumable sample vessel whose size and dimensions can vary widely, one convenient example of which is a vessel whose outer dimensions are similar to those of a microscope slide. The vessel can thus be similar in construction and dimensions to the vessel described in US 2006/0223165 A1 referenced above, with at least one flat, shallow internal chamber bounded on the top and bottom by flat, optically clear windows, which can be plastic sheets, whose spacing is close enough that most of the cells of the sample form a layer that is one cell deep. Appropriate inlet and vent ports can be included in the vessel to allow the chamber to be easily and completely filled with the sample. The vessel is then placed in the instrument where it intersects a linear optical path. The term "linear" as used herein denotes a path with no turns or other changes in direction of the light beams other than those caused by lenses. The vessel enters the instrument through a slot at a designated height in the optical path, and as described below in greater detail, the instrument in certain embodiments of the invention contains features that automatically adjust the height of the sample for purposes of focusing the sample image. Certain embodiments contain features that cause all instrument functions to begin operation upon the insertion of the sample vessel into the instrument.

DETAILED DESCRIPTION

The upper and lower optical windows between which the cell suspension is retained inside the sample vessel are close enough that the retained suspension is a thin film whose lateral dimensions, i.e., its exposed length and width, are at least an order of magnitude greater that its thickness. The entire exposed area (i.e., lateral dimensions) of the sample chamber or a laterally dimensioned portion thereof serves as a field of view that is projected onto a digital imaging sensor that contains at least about 4,000,000 (four million) pixels, or in certain embodiments from about 4,000,000 to about 10,000,000 pixels, with each pixel being no greater than about 2×2 μm (4 μm$^2$) in size, or from about 0.5×0.5 μm (0.25 μm$^2$) to about 2×2 μm (4 μm$^2$) in certain embodiments, and in certain of the latter from about 1×1 μm (1 μm$^2$) to about 2×2 μm (4 μm$^2$) The field of view imaged by the sensor is at least about 3 square millimeters, and often from about 3 mm$^2$ to about 110 mm$^2$. A complementary metal oxide semiconductor (CMOS) is one example of a digital imaging sensor useful for this purpose. Examples of CMOS sensors meeting these parameters are the OV5620 and OV5632 color imagers available from OmniVision, Santa Clara, Calif., USA. Other examples are available from Aptina Imaging, a division of Micron Technology, Inc., of San Jose, Calif., USA. A color digital imaging sensor can also be used. Image processing to count the cells in the image generated by the CMOS sensor can be achieved by known digital counting methods, such as those mentioned above.

The image of the sample chamber can be magnified along the optical path by a magnification that is often within a range of from about 1.5 to about 6, or a range of from about 1.5 to about 3, with a magnification of about 2 as an example. This can be achieved by a two-lens achromat assembly. An example of such a lens assembly is a lens of 35-mm focal length closest to the sample, a lens of 60-mm focal length closest to the sensor, and an aperture between the two lenses. The distance between the lens nearest the sample and the sample itself in this example is thus 35 mm, and the distance between the lens nearest the sensor and the imager itself is 60 mm. The magnification of the system is the ratio of the focal lengths of the two lenses, which in this case is 60 mm/35 mm=1.7. The two lenses can each for example be 12.5 mm in diameter, and the aperture can be 6 mm in diameter. Lenses of other diameters and focal lengths that will produce the same or approximately the same results will be readily apparent to those skilled in the art. The footprint of the instrument is defined as the area projected by the larger of the instrument and its support base on a plane perpendicular to the optical path. As noted above, the instrument can be constructed with a small footprint, particularly one that is less than 300 cm$^2$ in area.

When a flat digital imaging sensor is used, a negative lens can be positioned below the sensor to intercept the optical signal immediately and to correct the focus field curvature of the achromat lens pair. This type of field curvature is common in optical systems and is also referred to as Petzval curvature. In an illustrative embodiment, a 6 mm-diameter lens with a minus-18 mm focal length is used. The lens thickness can vary but is optimally selected to correct the curvature without substantially reducing the field of view.

Illumination of the sample can be achieved with a conventional light source at the base of the instrument and a collimating lens between the light source and the sample. With these components the sample is illuminated by trans-illumination without a diffuser. A preferred light source is a single white light-emitting diode (LED) with a fluorescent coating. An example of such a component is LUXEON® rebel White, part no. LXML-PWN1-0050, available from Philips Lumileds Lighting Company, San Jose, Calif., USA. An example of a collimating lens is one that is 9 mm in diameter with a focal length of 18 mm. With these dimensions and those of the preceding paragraphs, an instrument can be constructed with the achromat lens pair approximately 35 mm above the sample, and the sensor approximately 60 mm above the achromat lens pair. With an achromat lens pair having a thickness of approximately 13 mm, the total distance between the sample and the sensor can be as little as 108 mm. In general, the optical path of the instrument, i.e., defined herein as the arrangement of the components extending from the light source to the CMOS or other digital imaging sensor, can be 20 cm or less in height. In preferred instruments within the scope of this invention, the optical components are mounted to the housing interior in a floating manner using compliant counts, to avoid damage to, or misalignment of, the optical system upon jolts to the instrument, such as might occur when the instrument is dropped or mishandled, or collides with another instrument or piece of equipment.

As noted above, the sample vessel, which will be referred to henceforth as a sample slide in view of its similarity in size and shape to a microscope slide, is received in the instrument through a slot that is positioned at a location along the optical path that is at a distance from the nearest lens of the achromat lens pair equal to the focal length of the lens. In its preferred embodiments, the instrument as a whole is 30 cm or less in height, and the use of a digital imaging sensor as described above that employs a large number of pixels of the small sizes indicated permits the instrument to be constructed with the slot at a sufficient height to allow the user to comfortably insert the slot by hand, i.e., clearing the user's hand from the table on which the instrument rests. The slot can thus be 60 mm or more from the base of the instrument, and preferably 70-80 mm from the base.

In preferred embodiments of the invention, the instrument provides autofocusing of the sample image by automatically adjusting the height of the slide following its insertion. One means of autofocusing involves the use of an image processor chip that provides an output of image contrast within an array of zones across the image from the sensor. An example of such a chip is the Freescale Semiconductor MC9328MX21, available from Keil™—an ARM Company, Plano, Tex., USA; other examples will be apparent to those skilled in the art. The sum of the absolute differences of adjacent green pixels in a particular zone of the sensor array can be used as the image contrast value, and optimum focus is achieved when the image contrast value is at a maximum. The focus can then be adjusted by a geared motor connected to the slide mount within the receiving slot, i.e., the motor when rotated will move the slide mount up or down to change the focus of the image. The contrast value is detected at various positions of the motor which is then returned to the position producing the highest contrast value. In many embodiments of the instrument, this autofocusing can occur in 15 seconds or less.

An accessory that can be supplied with the instrument is a standard slide the quality control, such as verifying the accuracy of counting live and dead cells and the ability of the instrument to focus properly. The standard slide can have the same external dimensions as a sample slide, but instead of a sample chamber(s), the standard can have an array of dark-colored spots and rings printed on it, the spots simulating dead cells and detected as such in the digital imaging sensor and the rings simulating live cells and detected as such in the digital imaging sensor.

In certain embodiments of the concepts described herein, the functions performed by the instrument, including autofocusing and cell counting, are initiated by the simple insertion of the sample slide. This initiation can be achieved by the inclusion of a non-contact optical reflection sensor located within the slot or on the slide mount within the slot. An example of a suitable sensor is one that emits an infra-red beam and detects objects within approximately one millimeter of the sensor aperture by detecting a reflected signal from the beam. The reflected signal will rise to a maximum level when the slide is fully inserted, and the high signal will initiate the autofocusing and cell counting mechanisms. One example of a sensor that can serve this purpose is the QRE1113 Reflective Object Sensor, available from Fairchild Semiconductor Corporation, San Jose, Calif., USA. Other examples will be apparent to those skilled in the art.

A further feature that can be included in instruments embodying the features described herein is the automatic detection of cells in the sample that are stained with a vital stain. A vital stain is one that preferentially stains dead cells, and the differentiation between cells stained with such a stain and those that are not is achieved by the use of differently colored pixels. Trypan blue is one example of a vital stain; eosin and propidium iodide are other examples. Trypan blue transmits blue light and attenuates red light, and by comparing the intensities of blue and red pixels in the image sensor, the instrument can determine whether cells stained with a vital stain are present. Other dyes will afford similar color distinctions as appropriate to the dyes themselves. Image processing chips that incorporate this automatic detection feature include those referenced above and are readily available. The instrument can be programmed to eliminate any possible undercounting of viable cells and thereby detect viable cells to a particularly high degree of accuracy by focusing on two or more planes. The contrast between live cells and dead cells can be increased further by using optical filters to control the illumination bandwidth, or by selecting a spectrally narrow light source, such as an LED of a particular color instead of white. For example, a 585 nm optical filter with about 20 nm bandwidth can be used to match the illumination to the peak absorption wavelength of the Trypan blue dye, whose peak absorption is 586 nm. The dead cells will appear darker when the sample is illuminated through this filter.

In preferred instruments within the scope of this invention, all functions that contribute to the obtainment of a cell count in the sample are contained within the instrument housing, and the full operation of the instrument can thus be achieved without the use of an external machine or computer. Included among these functions are the automatic focusing by varying the height of the sample slide to find the best focal plane to discriminate cells from background, the determination of whether the sample has been stained with Trypan blue or other vital stain, a multi-focal plane analysis when a vital stain is detected so that each cell is scored on multiple focal planes to prevent undercounting of live cells, an integrated dilution counter to determine the volume of a cell suspension to use, the ability to produce a visual image of the cells on the display at the option of the user and to zoom in tier a detailed visual inspection of the cells, and the ability and user option to export the results to a USB flash drive or to a thermal printer or other external printer. All of these functions can be initiated by the simple insertion of the sample slide by way of the non-contact optical reflection sensor described above, and in many cases, the execution of these functions is completed in 30 seconds or less.

The Figures hereto depict an instrument that contains many of the features describe above and serves as one example of an implementation of the concepts described herein.

Figure 1:
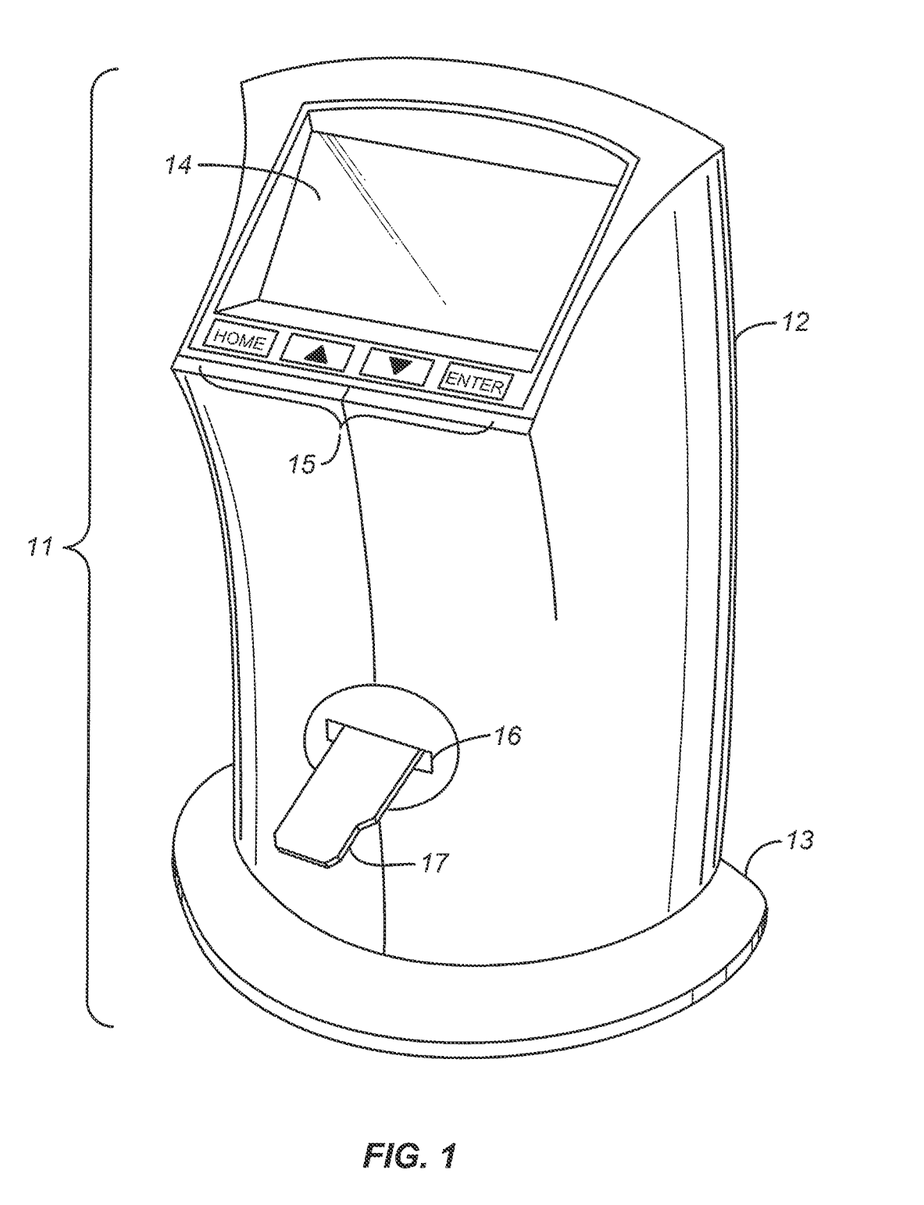
FIG. 1 is a perspective view of a cell counting instrument representing an example of an implementation of the concepts disclosed herein.

FIG. 1 depicts an automated cell counter instrument 11 in its upright position as it would be used on a laboratory bench. The visible parts of the instrument are a housing 12, a support base 13, a display screen 14, a control panel 15, and a slot 16 for insertion of a sample slide 17. The display screen shows the progress of the cell counting analysis, identifies the functions of the instrument as they are being performed, and offers options to the user for various functions and for showing an image of the cells in the sample slide.

Figure 2:
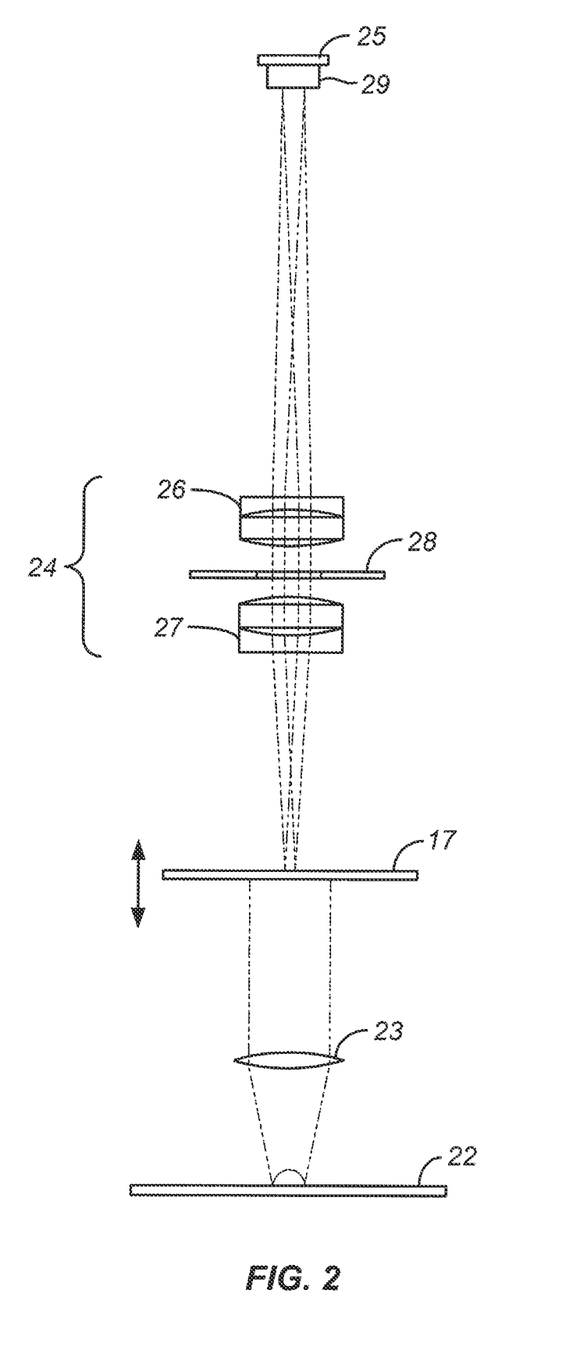
FIG. 2 is a diagram of the optical components of the instrument of FIG. 1.

FIG. 2 depicts components of the optical path in the interior of the instrument of FIG. 1 with the sample slide 17 having been positioned in the optical path. The sample slide 17 is horizontal and resides above an LED board 22 serving as the light source. A collimating lens 23 renders the light rays from the LED parallel as they approach the sample slide. The achromat lens pair 24 is positioned between the sample slide 17 and the sensor 25. The two lenses 26, 27 of the achromat lens pair are separated by an aperture 28. A field flattening lens 29 is positioned immediately below the sensor 25.

Figure 3:
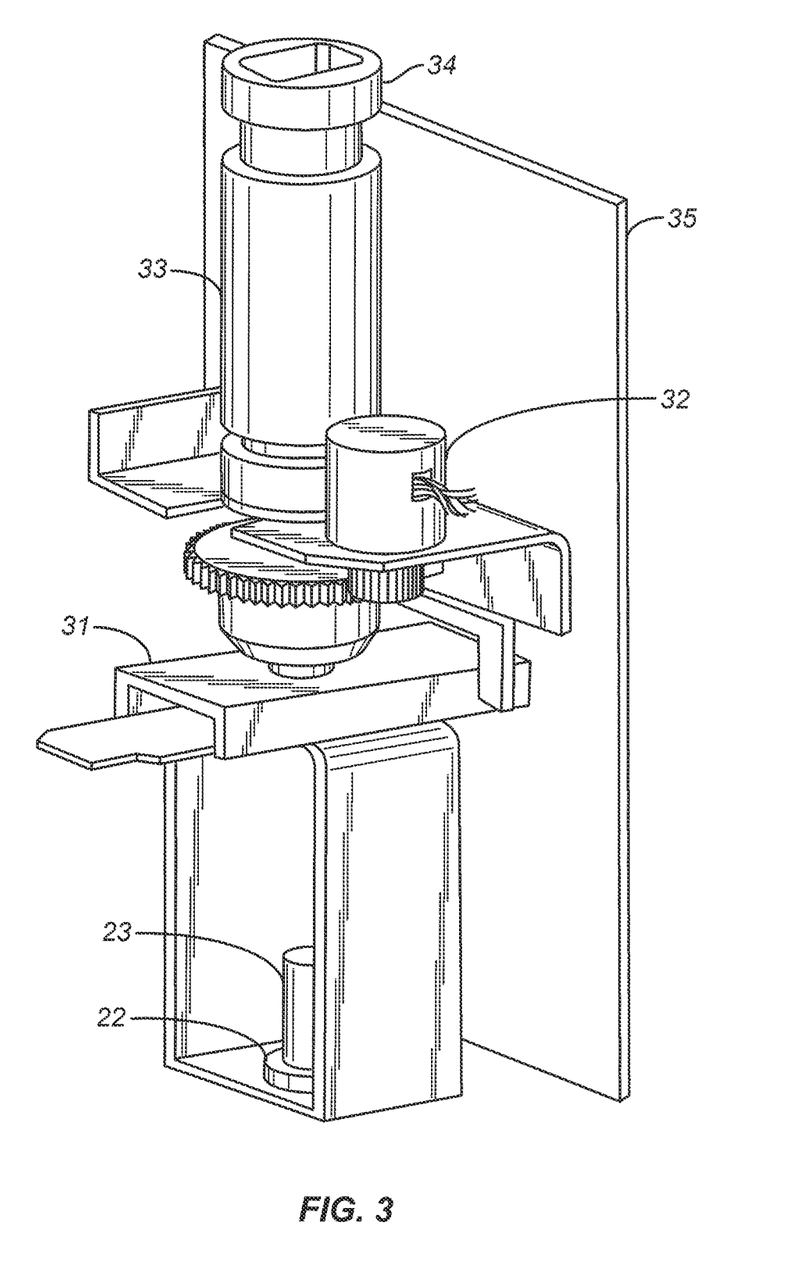
FIG. 3 is a perspective view of optical components in the interior of the instrument of FIG. 1.

FIG. 3 depicts the main optics assembly, showing the slide mount 31 with the sample slide 17 partially inserted, the LED board 22, the illumination (collimating) lens 23, the geared motor 32 that adjusts the slide height to focus the image, and an imaging lens tube 33 terminating in a fitting 34 to receive the CMOS sensor board. Also shown in the Figure is the main printed circuit board 35 that controls the functions of the instrument and includes a motor drive chip to control the motor 32. The board 35 resides within the housing and the position of the board in the Figure reflects its position relative to the optics assembly.

Figure 4:
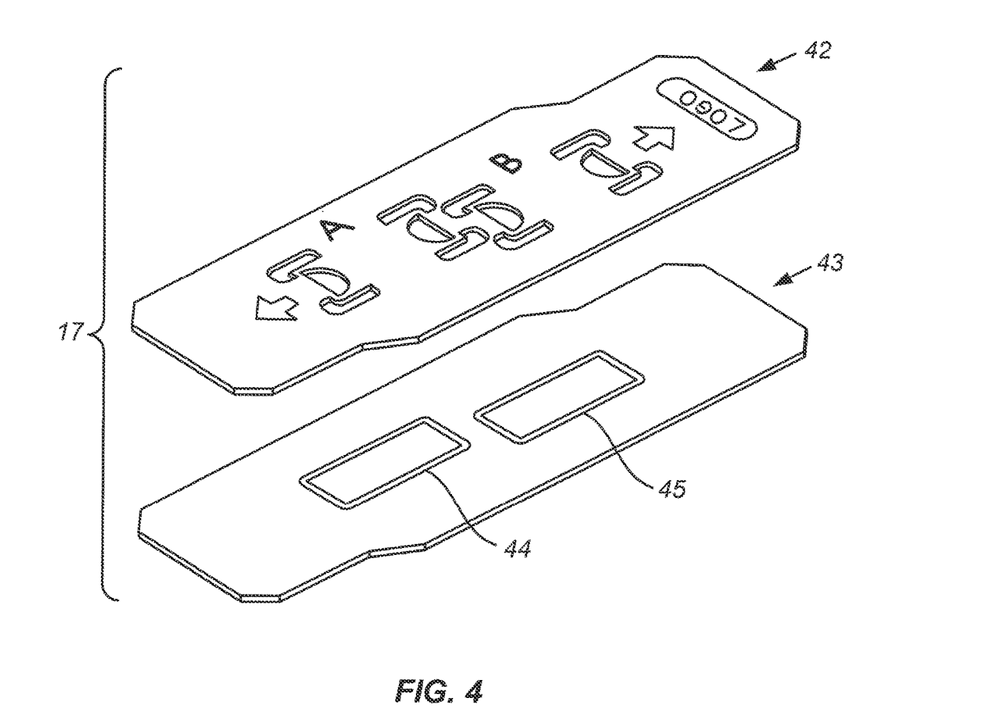
FIG. 4 is an exploded view, in perspective, of two plates constituting a sample slide for use in the instrument of FIG. 1.
Figure 5A:
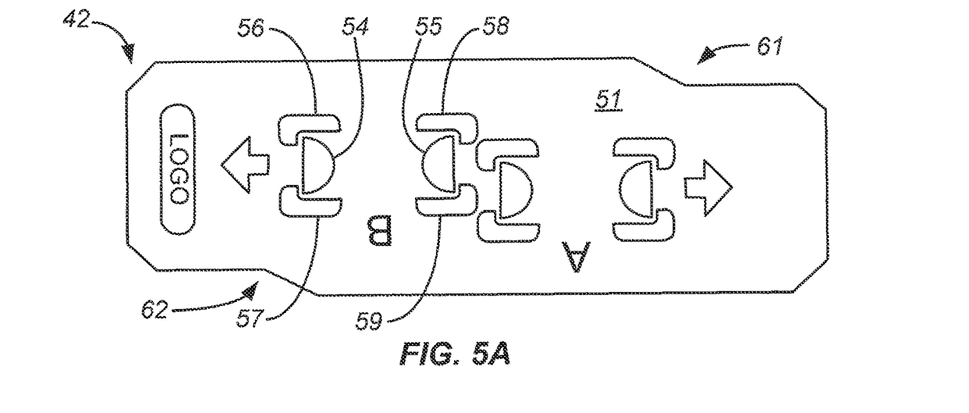
FIG. 5A is a view of the upper surface of the upper plate of the sample slide of FIG. 4.
Figure 5B:
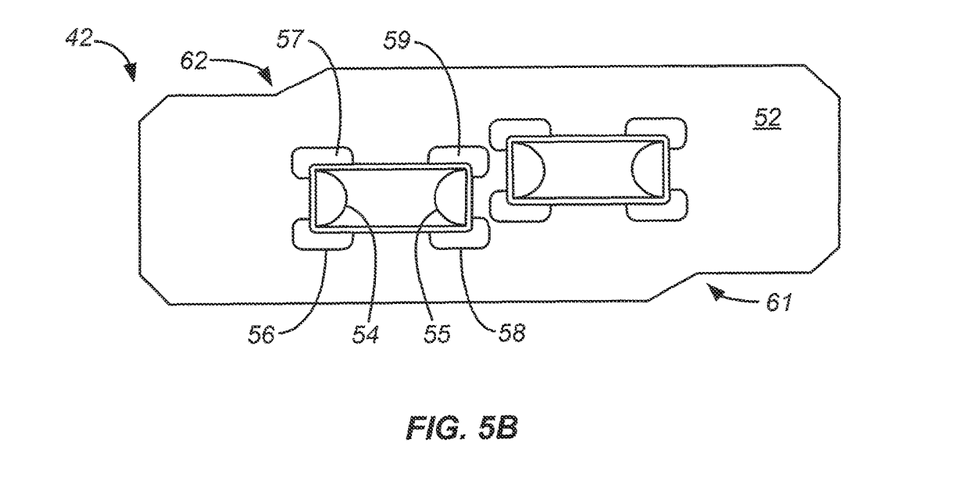
FIG. 5B is a view of the lower surface of the upper plate of the sample slide of FIG. 4.

A sample slide for use in the instrument of the preceding Figures is shown in FIGS. 4, 5A, and 5B. The view in FIG. 4 is a perspective view, and the slide 17 is formed of two plates 42, 43 bonded together but shown separated in the Figure. The slide contains two sample chambers, as indicated by the indicia "A" and "B," respectively, separated from each other lengthwise along the slide and laterally offset from each other. The areas 44, 45 of the lower plate 43 that form the bottom surfaces of the sample chambers are made of optically transparent material, as are the corresponding areas of the upper plate 42 that are directly above these areas on the lower plate and form the upper surfaces of sample chambers. The lower plate 43 in this embodiment is thicker than the upper plate 42 to provide rigidity to the slide, and the relative thinness of the upper plate 42 permits the upper window of each sample chamber to be thinner than the lower window, and indeed as thin as possible to achieve a highly focused image in the CMOS sensor. Each sample chamber is thus offset from the center plane of the slide and closer to the upper plate 42 than to the lower plate 43.

FIGS. 5A and 5B are planar views of the top surface 51 and bottom surface 52, respectively, of the upper plate 42, the bottom surface 52 being the surface that is bonded to the lower plate 43. Each sample chamber is defined by a recess 53 (FIG. 5B) in the bottom surface of the upper plate, which further reduces the thickness of the area forming the optically clear window at the top of each sample chamber. In one example of the dimensions of the slide, the thickness of the upper plate in areas other than the recess 53 is 0.65 mm and the thickness of the lower plate is 1.00 mm, for a total slide thickness of 1.65 mm. The recess 53 is 0.100 mm in depth, which thus forms a sample chamber that is 0.100 mm in depth, a standard sample chamber thickness for manual hemocytometers. Each sample chamber has two loading or vent ports 54, 55, one at each of the two opposing longitudinal ends of the elongated chamber. Overflow areas 56, 57, 58, 59 that are open at the top of the slide are positioned at each of the four corners of each sample chamber to accommodate excess sample and thereby insure that the sample chamber is properly filled with sample.

Since each sample chamber is closer to the upper plate 42 than to the lower plate 43, the slide functions best when properly inserted into the cell counter with the upper plate 42, and hence the thinnest optical window, at the top. To ensure that the slide is inserted in this orientation, the slide is formed with notches 61, 62 in two diagonally opposing corners of the slide. The internal surfaces of the slot in the cell counter into which the slide is inserted to initiate the functions of the cell counter contains contour features that are complementary to these notches. The notches and complementary contours in the slot thereby prevent the user from inserting the slide upside down, i.e., with the upper plate 42 at the bottom rather than the top. The symmetrical arrangement of the notches also complements the symmetrical arrangement of the two sample chambers and permits the slide to be inserted with either end first, while preventing the slide from being inserted in an inverted position (upside down). Since the slide is preferably a consumable item, it can thus be used for cell counting measurements on two independent samples at different times, and once both chambers have been used the slide can be disposed of and not used again.

Variations on the construction of the sample slide that still ensure proper orientation will be readily apparent to those skilled in the art. The arrangement, number, and shapes of the notches can thus be varied, as can the number of sample chambers and their locations relative to each other in the slide. The material of construction can vary widely and can be any material that can form an optically clear window, that is inert to the sample, and that is sufficiently rigid to be inserted into the cell counter. Poly(methyl methacrylate) and polycarbonate are examples of materials that are can be used. Others will be readily apparent to those skilled in the art. Likewise, the bonding of the plates can be accomplished by conventional means. Laser welding and ultrasonic welding are examples.

In the claims appended hereto, the terms "a" and "an" are intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A sample slide for counting cells in a cell suspension, said sample slide comprising:
   a flat plate with an internal chamber bounded by optically clear upper and lower windows, wherein the internal chamber has at least one overflow area positioned at a corner of the internal chamber, wherein the at least one overflow area is open at the top of said sample slide, wherein the internal chamber has a loading port and a vent port, and wherein the loading port and the vent port are at two opposing longitudinal ends of the internal chamber; and
   a first and a second orientation notch in said flat plate, wherein the first and second orientation notches are in diagonally opposing corners of said flat plate, and wherein the first and second orientation notches guide said flat plate into a cell counting instrument in an orientation whereby said upper window faces a selected direction within said instrument.

2. The sample slide of claim 1 wherein said upper window is substantially thinner than said lower window.

3. The sample slide of claim 1 comprising a single flat plate with first and second internal chambers therein, said internal chambers positioned laterally relative to each other in said flat plate and each having optically clear upper and lower windows, wherein the first and second internal chambers each have at least one overflow area positioned at a corner of each internal chamber, wherein the first and second internal chambers each have a loading port and a vent port, and wherein the loading port and the vent port of each internal chamber are at two opposing longitudinal ends of the internal chamber, said single flat plate comprising first and second orientation notches to guide said flat plate into said cell counting instrument in orientations whereby said optically clear upper windows face a selected direction within said instrument.

4. The sample slide of claim 3, wherein the first and second internal chambers are laterally offset from a center plane.

5. The sample slide of claim 3, wherein each of the first and second internal chambers has an overflow area positioned at each corner of each the internal chamber.

6. The sample slide of claim 3, wherein the orientation notches are symmetrical.

7. The sample slide of claim 3, wherein the orientation notches are asymmetrical.

8. The sample slide of claim 3, wherein the first and second orientation notches prevent incorrect insertion of the sample slide into the cell counting instrument.

9. The sample slide of claim 3, wherein the sample slide has more than one orientation notch on one side of the sample slide.

10. The sample slide of claim 3, wherein the orientation notches on either side of the sample slide have varied shapes.

11. The sample slide of claim 1, wherein the internal chamber is laterally offset from a center plane.

12. The sample slide of claim 1, wherein the sample slide is constructed of a material comprising poly(methyl methacrylate) or polycarbonate.

13. The sample slide of claim 1, wherein the orientation notch prevents incorrect insertion of the sample slide into the cell counting instrument.

14. The sample slide of claim 1, wherein the sample slide has a total thickness of about 1.65 mm.

15. The sample slide of claim 1, wherein the flat plate comprises a lower plate having a thickness of about 1.00 mm.

16. The sample slide of claim 1, wherein the flat plate comprises an upper window having a thickness of about 0.65 mm.

17. The sample slide of claim 1, wherein the sample chamber is defined by a recess of about 0.100 mm in depth.

18. The sample slide of claim 1, wherein the internal chamber has an overflow area positioned at each corner of the internal chamber.

* * * * *